(12) United States Patent  (10) Patent No.: US 7,710,262 B2
Ruha  (45) Date of Patent: *May 4, 2010

(54) SENSOR DATA SHARING

(75) Inventor: Antti Ruha, Oulu (FI)

(73) Assignee: Nokia Corporation, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 11/944,807

(22) Filed: Nov. 26, 2007

(65) Prior Publication Data

US 2008/0117039 A1   May 22, 2008

Related U.S. Application Data

(63) Continuation of application No. 10/943,481, filed on Sep. 17, 2004, now Pat. No. 7,319,385.

(51) Int. Cl.
*G08B 1/08* (2006.01)
(52) U.S. Cl. ................................. 340/539.12
(58) Field of Classification Search ............ 340/539.12, 340/573.1, 384.1; 455/456.1, 414.1; 600/300
See application file for complete search history.

(56) References Cited

U.S. PATENT DOCUMENTS

| | | | |
|---|---|---|---|
| 5,524,637 A | 6/1996 | Erickson | |
| 5,724,265 A | 3/1998 | Hutchings | |
| 6,018,677 A | 1/2000 | Vidrine et al. | |
| 6,463,385 B1 | 10/2002 | Fry | |
| 6,501,386 B2 | 12/2002 | Lehrman et al. | |
| 6,554,773 B1 | 4/2003 | Nissila et al. | |
| 6,840,904 B2* | 1/2005 | Goldberg | 600/300 |
| 6,874,029 B2 | 3/2005 | Hutcheson et al. | |
| 2002/0067256 A1* | 6/2002 | Kail, IV | 340/539 |
| 2004/0059205 A1 | 3/2004 | Carlson et al. | |
| 2004/0105534 A1* | 6/2004 | Dezonno | 379/114.13 |
| 2005/0088296 A1* | 4/2005 | Lee | 340/539.12 |
| 2005/0171410 A1* | 8/2005 | Hjelt et al. | 600/300 |
| 2007/0213126 A1 | 9/2007 | Deutsch et al. | |

FOREIGN PATENT DOCUMENTS

| | | |
|---|---|---|
| EP | 1 066 867 A2 | 10/2001 |
| EP | 1 186 272 A1 | 3/2002 |
| GB | 2 339 833 A | 2/2000 |

* cited by examiner

*Primary Examiner*—Phung Nguyen
(74) *Attorney, Agent, or Firm*—Ditthavong Mori & Steiner, P.C.

(57) ABSTRACT

The disclosed embodiments relate to a method for operating two or more mobile terminals in an interactive session. The mobile terminals are provided with one or more sensors. The data captured by the sensors is sent via a wireless connection to the other mobile terminals that participate in the interactive session. The data received from the other mobile communication terminals is communicated to the user of the respective mobile communication terminals via the user interface.

19 Claims, 3 Drawing Sheets

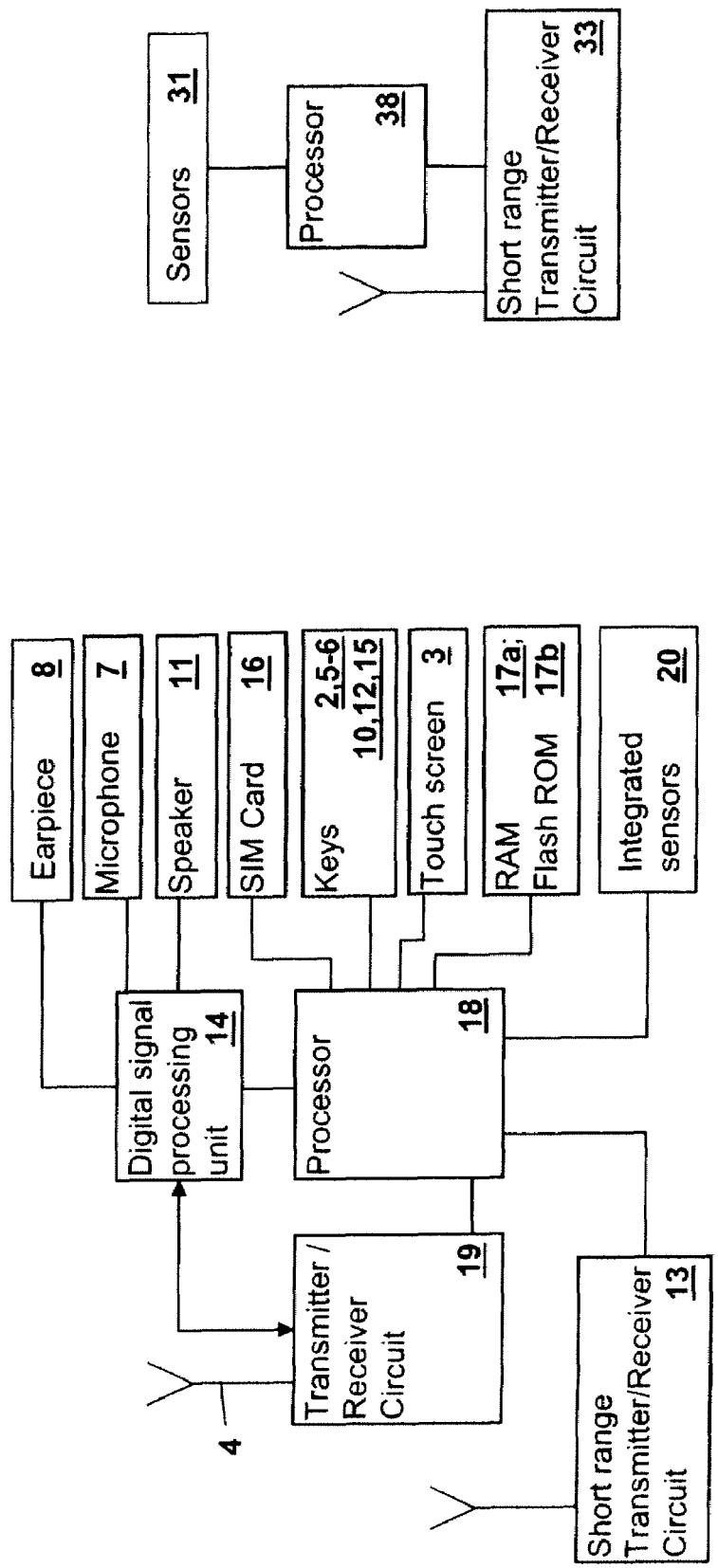

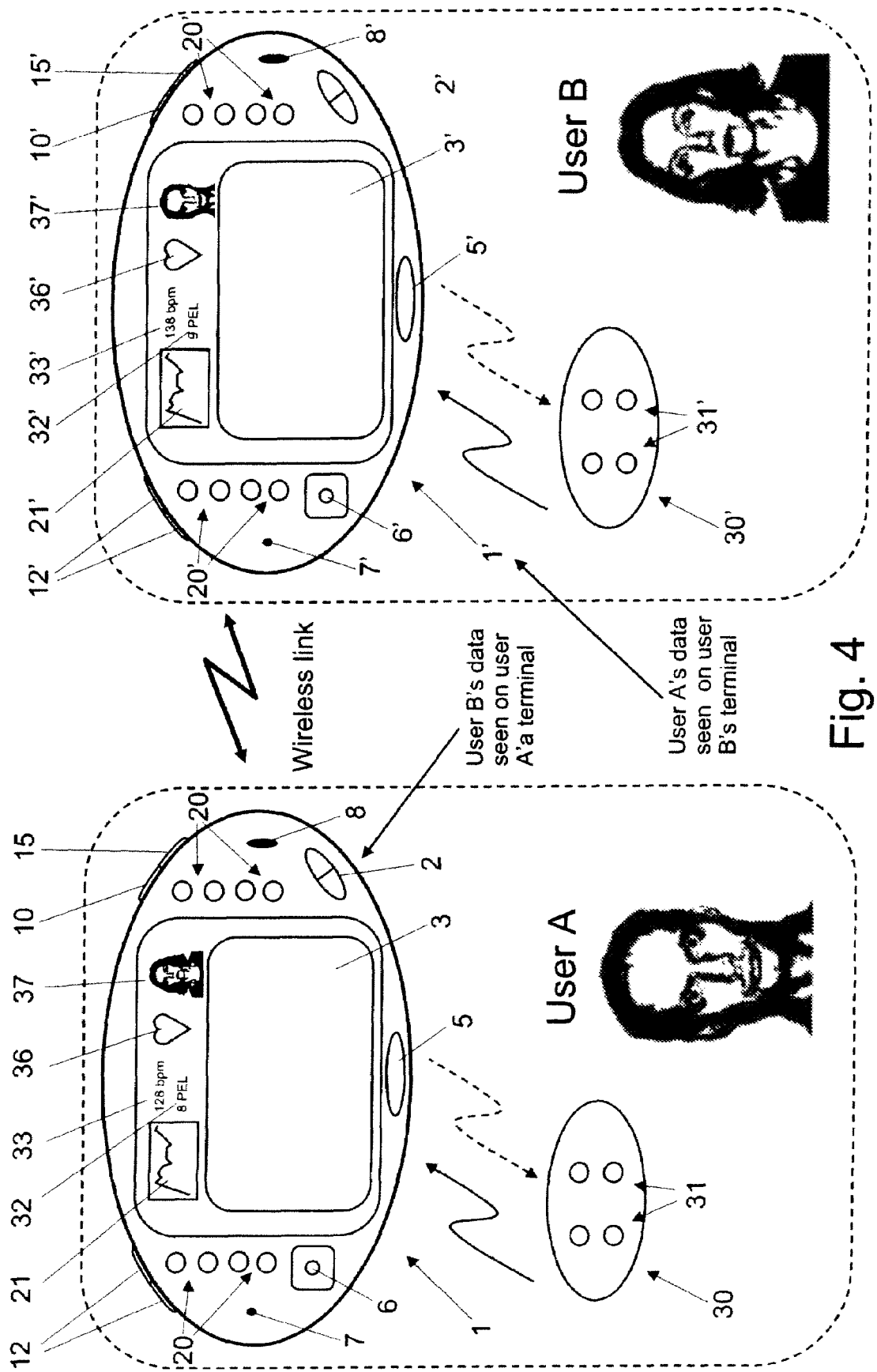

SENSOR DATA SHARING

CROSS-REFERENCE TO RELATED APPLICATIONS

This application is a continuation of, and claims priority to, U.S. patent application Ser. No. 10/943,481, filed on Sep. 17, 2004, now allowed.

BACKGROUND

1. Field

The present invention relates to interactive operation of at least two mobile communication terminals.

2. Brief Description of the Related Developments

Mobile communication terminals have in the recent past undergone a tremendous increase in the range of features offered by the individual models. Mobile communication terminals are increasingly being used for entertainment, gaming, in sports, etc.

One of the applications is interactive gaming. Previously, this interactive gaming has been relegated to users who are hard-core computer enthusiasts. For instance, online gaming required arcane skills belonging only to computer savvy users. However, online gaming has become easier for the more casual user. In fact, online gaming is rapidly becoming one of the most popular activities on the Internet.

The Nokia N-Gage® and N-Gage QD® provide game and phone functionality and include advanced gaming and phone functionality. The N-Gage terminals provide mobile multi-player gaming with no cables or wires. Most of the games available for the terminals include multiplayer options for 2 and/or up to 4 players, either via Bluetooth® wireless technology within a distance of 10 meters or over GPRS, which offers the possibility for gaming over a wide-area network.

EP 1 066 867 discloses a method of connecting a plurality of mobile phones together to a game server through a network for playing a game, setting up a game scenario for each of the plurality of mobile phones and transmitting game signals between the plurality mobile phones across the network. At least two of the plurality of mobile phones are remotely located.

Multiplayer functionality has greatly enhanced the attractiveness of mobile gaming since artificial opponents cannot match human opponents. There is a continuous strive in the field to improve the gaming experience despite the improvements in imagines, sound, gameplay and multiplayer capacity in recent history.

There is thus, a need for an improved gaming experience in mobile terminals.

The Nokia 5140® provides a sports oriented phone that can be used in combination with the POLAR 625X® wrist-worn running computer. The POLAR 625X® running computer records running speed and distance measurement with heart rate and stores the data of a training session in the wrist unit. After completing the training session the data is transferred via IR to the Nokia 5140® mobile phone. The training data can then be reviewed stored and send with the Nokia 5140® mobile phone.

Sports training is often more effective and enjoyable with a partner or in a group. For practical reasons it is however not always possible for the partners to train in one and the same location. There is therefore a need for an interactive system to improve training conditions when partners cannot train in one and the same location.

SUMMARY

The present invention provides a method for interactive operation of at least two mobile communication terminals comprising the steps of: providing a first mobile communication terminal with at least one sensor coupled thereto, providing a second mobile communication terminal and at least one sensor coupled thereto, the first terminal capturing data from the at least one sensor coupled thereto, the second terminal capturing data from the at least one sensor coupled thereto, the first terminal sending the captured sensor data via a wireless connection to the second terminal, the second terminal sending the captured sensor data via a wireless connection to the first terminal, the first terminal presenting an indication of the data received from the second terminal, and the second terminal presenting an indication of the data received from the first terminal.

BRIEF DESCRIPTION OF THE DRAWINGS

In the following detailed portion of the present description, the invention will be explained in more detail with reference to the exemplary embodiments shown in the drawings, in which

FIG. 2 is a block diagram illustrating the general architecture of a mobile phone in accordance with the present invention;

FIG. 3 is a block diagram illustrating the general architecture of a sensor unit in accordance with the present invention; and FIG. 4 is a block diagram of an interactive session of two mobile phones.

DETAILED DESCRIPTION OF THE EMBODIMENT(S)

Figure 1:
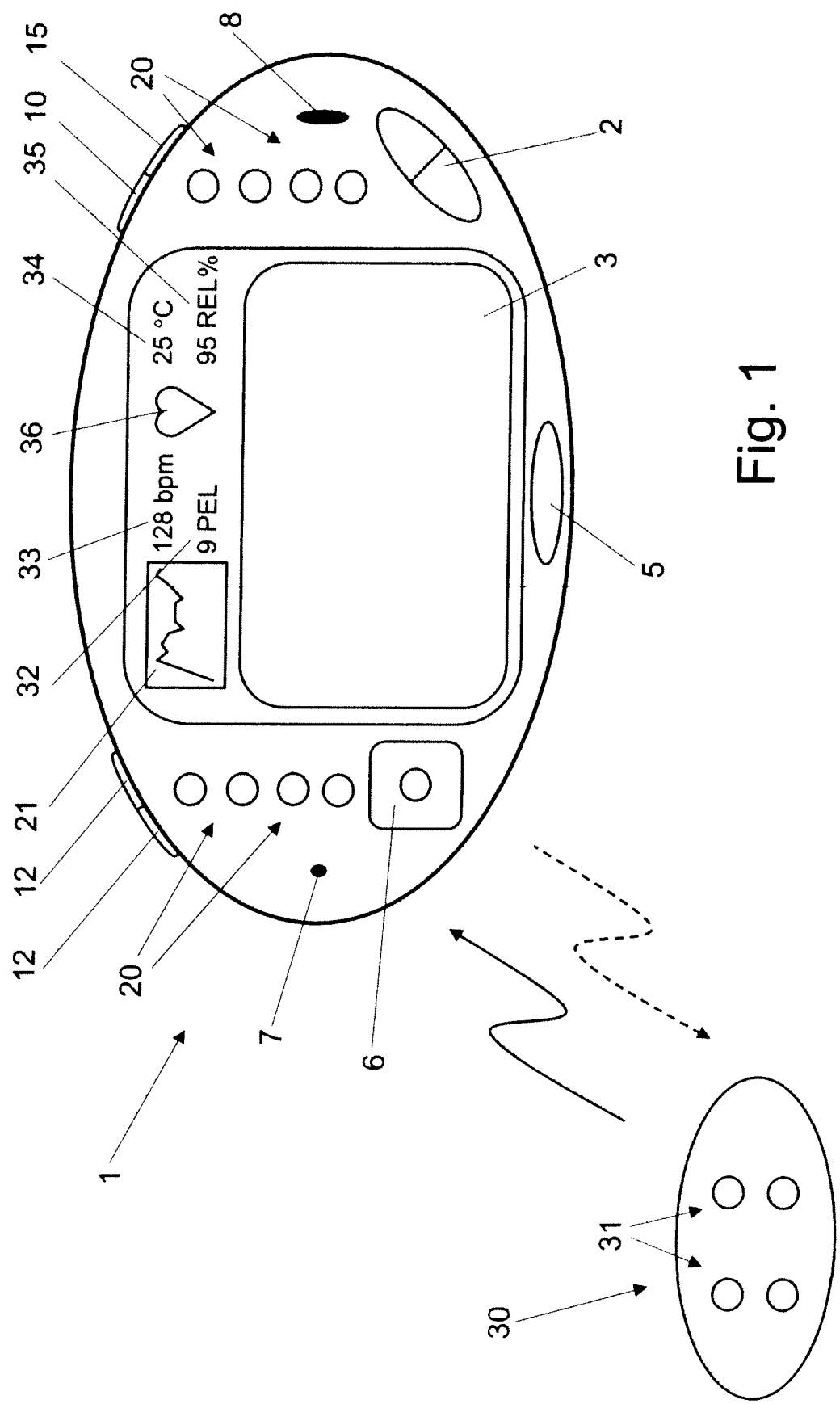
FIG. 1 is a front view of a mobile phone and a sensor unit coupled thereto.

In the following detailed description, a mobile communication terminal according to the invention in the form of a hand portable phone, preferably a cellular/mobile phone, will be described by the preferred embodiments. The term mobile communication terminal as used here includes all hand portable terminals provided with a form of wireless or wired connection to a network or other terminal. Another example of such a terminal could be a PDA with a Wi-Fi® capability.

Referring now to FIG. 1 a mobile phone 1 according to a preferred embodiment of the invention is disclosed. The mobile phone 1 has a housing, a zoom and switch key 2, a stylus operated touch screen 3, an on/off button (not shown), a clear key 5, an earpiece 8 (only the openings are shown), a hands free speaker 11 (not shown in FIG. 1), a microphone 7 (only the opening is shown), a charger connector (not shown), and a Pop-Port™ (not shown). The phone 1 according to the preferred embodiment is adapted for communication via a cellular network, such as the GSM 900/1800 MHz network, but could just as well be adapted for use with a Code Division Multiple Access (CDMA) network, a 3G network, or a TCP/IP-based network (e.g. via WLAN, WIMAX or similar).

The mobile phone has a flat touch sensitive display 3 that is typically made of an LCD with optional back lighting, such as a TFT matrix capable of displaying color images.

A releasable rear cover (not shown) gives access to the rechargeable battery pack (not shown) in the back of the phone that supplies electrical power for the electronic components of the mobile phone.

A number of sensors 20 are embedded in the mobile phone 1. Their size, shape and placement in the Figs. is purely diagrammatic, and does not correspond to size, shape and placement of the sensors that will actually be used. The size, shape and placement of each of the actual sensors depends completely on the type of sensor.

The toggle type zoom and switch key 2 is disposed on the right hand side of the display 3. The function of this key depends on the application and the current view. When applicable, this key makes the zoom option available, and enables switching between different views in an application. When using the earpiece, pressing this keys is used to increase or decrease the volume level, respectively. The zoom and switch key 2 is also used for playing games. A four-way plus select key 6 is disposed to the left of the display and can be used for cursor movement, scrolling and selecting.

The mobile phone is additionally provided on its top with call handling keys 12 (on-hook and off-hook), a menu key 10, and a desktop key 15. The two call handling keys 12 are used for establishing a call or a conference call, terminating a call or rejecting an incoming call. The menu key 10 gives direct access to the menu, repeated presses moves between dialog pages. The desktop key 15 opens the desk application, which is the main view for the terminal.

There are two ways to enter text (letters, numbers and special characters) for entering a telephone number, write a text message (SMS, MMS, e-mail), write a name (associated with the phone number), etc. The first way is by writing characters directly onto the touchscreen 3 using the stylus (not shown). Handwriting recognition software transforms the handwriting into characters. The second way is by tapping the characters of an on-screen keyboard displayed on the touchscreen.

FIG. 1 also shows a remote sensor unit 30 as a wrist unit that includes sensors 31. The remote sensor could be a running computer or the like with its own display and user interface, or as shown a sensor unit included in a short range (Bluetooth®) wireless transmitter.

FIG. 2 illustrates, in block diagram form, the hardware architecture of a mobile phone 1 constructed in accordance with the present invention. A processor 18 controls the communication with the cellular network via the transmitter/receiver circuit 19 and an internal antenna 4. A microphone 7 transforms the user's speech into analogue signals, the analogue signals formed thereby are A/D converted in an A/D converter (not shown) before the speech is encoded in a digital signal processing unit 14 (DSP). The encoded speech signal is transferred to the processor 18, which e.g. supports the GSM terminal software. The processor 18 also forms the interface to the peripheral units of the apparatus, including a RAM memory 17a and a Flash ROM memory 17b, a SIM card 16, the touchscreen 3, the Pop-Port™, the sensors 20, the short range (Bluetooth®) transmitter/receiver 13 and the keys 2, 5-6, 10, 12, 15 (as well as data, power supply, etc.). The digital signal-processing unit 14 speech-decodes the signal, which is transferred from the processor 18 to the earpiece 8 or the hands free speaker 11 via a D/A converter (not shown).

FIG. 3 illustrates, in block diagram form, the hardware architecture of a remote sensor unit 30 constructed in accordance with the present invention. A processor 38 controls the communication via the short range transmitter receiver unit 33. The processor 38 forms the user interface for the sensors 31 (as well as power supply, RAM/ROM etc.). When the remote sensor unit 30 is active it sends data collected by the sensors 31 at intervals via the short range transmitter/receiver 33 to the short range transmitter/receiver 13 in the mobile phone.

The integrated sensors 20 and the sensors 31 in the remote sensor unit 30 can in dependence of application comprise sensors that measure ambient parameters, such as air temperature sensors, air humidity sensors, air pressure sensors, altimeters and air speed sensors and sensors that measure physical parameters of the user's body, such as body temperature sensors, heart rate sensors, blood pressure sensors, breathing rate sensors, perspiration sensors and movement sensors.

Referring now to FIG. 4, the mobile phone 1 of a user A is supplied with data from the remote sensor unit 30 via a Bluetooth® short range radio link and/or with sensor data from its embedded sensors 20. The sensor data is sampled at intervals, the sampling frequency depending on the parameter to be measured and the application in which the sensor data is to be used. The remote sensor unit 30 sends the sampled data to the mobile phone 1 at intervals that are short enough to guarantee a sufficient data input rate to the mobile phone 1.

The mobile phone 1 of user A is in wireless connection with a mobile phone 1' of user B. The wireless connection between mobile phone 1 and mobile phone 1 can be a Bluetooth® link if the devices are in short range from one another, or a link via the before mentioned type of wireless networks. The link between the mobile phones can be a client to client link or a link via a server. A server based link that could be used is disclosed in EP 1 066 967, hereby incorporated by reference.

When the sensor data from mobile phone 1 are received in mobile phone 1' they are shown on its display or presented in audible form via the earpiece or hands free speaker.

At the same time, mobile phone 1' has been receiving sensor data from its sensor unit 30' and/or sensor data from its embedded sensors 20' in the same way as described for mobile phone 1. Mobile phone 1 sends the sensor data that it receives from its sensor unit 30' via the wireless link to mobile phone 1.

When the sensor data from mobile phone 1' are received in mobile phone 1 they are shown on the display of mobile phone 1, or presented in audible form via the earpiece or hands free speaker.

In the present embodiment, two mobile phones 1,1' have been shown for illustrative purposes. This and all other embodiments can however be extended to any desirable higher number of users and mobile phones. In case of very high numbers of users the display 3 is not large enough to represent the data properly. The sensor data is in this case represented by calculating the parameter average of the users, i.e. the average heart rate 33 of the users involved is displayed. Teams of a plurality of users/mobile phones can be formed. The average heartbeat or other parameter for a team is displayed in the respective mobile phones. Instead, or in addition to the average values for a plurality of users, the zoom and switch key 2 or the four-way plus select key 6 can be used to toggle between the individual user's parameters.

In the preferred embodiment illustrated in FIG. 1, the sensors 20 and 31 pick up the users heart rate, the ambient air temperature and the ambient air humidity. The mobile phones 1 and 1' display the heart rate 33, a timeline graph of the heart rate 21, a heart blinking in tact with the respective user's heart rate 36, the air temperature 34 and the relative air humidity 35 and the personal excitement level (PEL) 32 on the touchscreen 3.

In the preferred embodiment shown in FIG. 4 the mobile phones 1 and 1' display the heart rate 33, a timeline graph of the heart rate 21, a heart 36 blinking in tact with the respective user's heart rate 33, a picture of the other user and the personal excitement level (PEL) 32 on the touchscreen 3.

The PEL 32 is calculated from a lookup table 1 shown below.

TABLE 1

| Heart rate | Air temp. | | | |
|---|---|---|---|---|
| | 0° C. | 15° C. | 25° C. | 35° C. |
| 70-90 BPM | 1 | 1 | 2 | 3 |
| 90-110 BPM | 2 | 2 | 3 | 4 |
| 110-130 BPM | 3 | 3 | 4 | 5 |
| 130-150 BPM | 4 | 5 | 6 | 7 |
| 150-170 BPM | 6 | 7 | 8 | 9 |
| 170-190 BPM | 8 | 8 | 9 | 10 |

The PEL could in dependence of the types of available sensor data take account of further parameters such as perspiration level, breathing rate, blood pressure wind and sun conditions, etc. The table could also take into account the users age, health, etc., as disclosed in EP1402817, hereby incorporated by reference to obtain a exercise stress level.

Heart rate 32 is measured from a person's skin on the basis of an electrocardiographic (ECG) signal produced by a heartbeat. Further information on ECG can be found in Human Physiology and Mechanisms of Disease by Guyton, Arthur C., Third Edition, Chapter 13: The Electrocardiogram, W.B. Saunders Company 1982, ISBN 4-7557-0072-8, which is incorporated herein by reference. An electrocardiographic signal is an electromagnetic signal produced by the heartbeat, detected on the body of a person to be measured. The signal is measured using electrodes that at least at two points come into contact with the body. In practice, an electrode nearest to the heart on a polarization vector usually operates as the actual measuring electrode while another electrode provides ground potential, a voltage measured by the measuring electrode being compared to the ground potential as a function of time. Publication U.S. Pat. No. 6,018,677, which is incorporated herein by reference, discloses a method and apparatus for measuring heart rate on the basis of a measured ECG signal. FIG. 3A in patent application GB 2 339 833 discloses a solution for positioning electrodes in a electrode belt. According to what has been disclosed in the publication, the electrode belt is placed on the chest while electrodes to be arranged against the chest measure the ECG signal produced by the heartbeat. More user friendly is a solution without an electrode belt, as disclosed in EP 1 186 272, hereby incorporated by reference. A heart rate sensor that can be used with the present invention is the sensor that is used in the Polar 625X® wrist type running computer, manufactured and sold by Polar Electro Oy, Kempele, Finland.

A blood pressure sensor that can be used in connection with the present invention is disclosed in U.S. Pat. No. 6,554,773, hereby incorporated by reference.

According to a preferred embodiment an interactive exercising application for managing and controlling sports training activates of sportsmen is running on mobile phone 1 and mobile phone 1'. The exercising application instructs the users to perform exercises in accordance with a training program, that is either preprogrammed or assembled from a user selection. The exercising program instructs the users via the display 3 and the hands free loudspeaker which exercises should be carried out. The users confirm the completion of an exercise via the user interface. The training program synchronizes the training activities of the users involved via a server connected to the wireless network. Thus, the exercising program will wait, until all participants have confirmed that they have completed the ongoing exercise before issuing the instructions for the next exercise.

During the training session the training partners can talk to one another via the mobile phones and see and/or hear the sensor data of their training partner, and realize that their training partner is also working out hard, thus stimulating the user to maintain or increase his/her own efforts. Thus, a similar encouraging effect as in training with a partner in the same location is obtained.

According to another embodiment, a gaming application is running on the mobile terminals. The gaming application could be any type of game that is multiplayer suitable, e.g. action, arcade, boardgames, adventure & role playing games, simulations, sports, strategy or wargames.

A method of playing games between clients of entities at different locations is known from EP 1 066 867, hereby incorporated by reference.

The user's game moves are send together with the sensor data to the other mobile phone. The gaming experience in e.g. bluff poker is enhanced in that it is possible to observe the other user's reaction to a game event. A poker heart rate and/or poker perspiration rate replaces the poker face.

The wireless connection between the mobile phones may established via infrared (IR) transmission from IR apparatus included as part of each mobile terminal, by a call being placed through the wireless telecommunications system between mobile terminals, by a Short Message Service (SMS) message which is transmitted by a Short Message Service Center (SMSC) of the wireless telecommunications system, by GPRS or by short range radio apparatus which operates according to the Bluetooth Standard.

Thus, while the preferred embodiments of the devices and methods have been described in reference to the environment in which they were developed, they are merely illustrative of the principles of the inventions. Other embodiments and configurations may be devised without departing from the scope of the appended claims.

The invention claimed is:

1. A method comprising:
   providing a mobile communication terminal with at least one sensor coupled thereto;
   capturing data in the terminal from the at least one sensor;
   sending the captured data to at least one other mobile communication terminal while receiving other sensor data from the at least one other mobile communication terminal; and
   presenting an indication of the received other sensor data via a display or loudspeaker of the mobile communication terminal,
   wherein the mobile communication terminal is in a gaming session in which gaming data is exchanged between the mobile communication terminal and the at least one other terminal, and the sensor data is corresponded to and included in the gaming data.

2. The method according to claim 1, further comprising:
   displaying received gaming data corresponding to the sensor data; and
   detecting a reaction to a game event of a user of the at least one other mobile communication terminal.

3. The method according to claim 2, wherein the sensor data include physical parameters of a body of the user.

4. The method according to claim 3, wherein the physical parameters include a heart rate and a perspiration rate.

5. The method comprising:
   providing a mobile communication terminal with at least one sensor coupled thereto;
   capturing data in the terminal from the at least one sensor;

sending the captured data to at least one other mobile communication terminal while receiving other sensor data from the at least one other mobile communication terminal; and presenting an indication of the received other sensor data via a display or loudspeaker of the mobile communication terminal, wherein the mobile communication terminal is in a sports training session in which training data is exchanged between the mobile communication terminal and the at least one other terminal, and the sensor data is included in the training data.

6. The method of claim 5, wherein the at least one sensor is embedded in the mobile communication terminal or located remotely from the mobile communication terminal.

7. The method of claim 5, wherein the indication is a number and/or a graph presented on the display of the mobile communication terminal.

8. The method of claim 5, further comprising that the captured data from the at least one terminal is transmitted from the terminal to the at least one other terminal simultaneously with receiving the other sensor data from the at least one other terminal.

9. The method of claim 5, further comprising the at least one other terminal presenting an indication of data received from the mobile communication terminal.

10. The method of claim 5, wherein said at least one sensor measures ambient parameters.

11. The method according to claim 10, wherein said at least one sensor comprises air temperature sensors, air humidity sensors, air pressure sensors, altimeters or air speed sensors.

12. The method according to claim 5, wherein said at least one sensor measures physical parameters of the user's body.

13. The method according to claim 12, wherein said at least one sensor comprises body temperature sensors, heart rate sensors, blood pressure sensors, breathing rate sensors, perspiration sensors or movement sensors.

14. The method according to claim 5, wherein the received data from one sensor is processed and presented in a graph shown on the display.

15. The method according to claim 5, wherein the received other sensor data is received from several sensors and is combined, processed and presented, as derived parameter on the display.

16. A computer-readable storage medium carrying one or more sequences of one or more instructions which, when executed by one or more processors, cause a mobile communication terminal to at least perform the following steps:
coupling with at least one sensor thereto;
capturing data from the at least one sensor;
sending the captured data to at least one other mobile communication terminal while receiving other sensor data from the at least one other mobile communication terminal; and
presenting an indication of the received other sensor data via a display or loudspeaker of the mobile communication terminal,
wherein the mobile communication terminal is in a sports training session in which training data is exchanged between the mobile communication terminal and the at least one other terminal, and the sensor data is included in the training data.

17. A mobile communication terminal comprising:
at least one processor; and
at least one memory including computer program code,
the at least one memory and the computer program code configured to, with the at least one processor, cause the mobile communication terminal to perform at least the following,
couple with at least one sensor thereto;
capture data from the at least one sensor;
send the captured data to at least one other mobile communication terminal while receiving other sensor data from the at least one other mobile communication terminal; and
present an indication of the received other sensor data via a display or loudspeaker of the mobile communication terminal,
wherein the mobile communication terminal is in a sports training session in which training data is exchanged between the mobile communication terminal and the at least one other terminal, and the sensor data is included in the training data.

18. A computer-readable storage medium carrying one or more sequences of one or more instructions which, when executed by one or more processors, cause a mobile communication terminal to at least perform the following steps:
coupling with at least one sensor thereto;
capturing data from the at least one sensor;
sending the captured data to at least one other mobile communication terminal while receiving other sensor data from the at least one other mobile communication terminal; and
presenting an indication of the received other sensor data via a display or loudspeaker of the mobile communication terminal,
wherein the mobile communication terminal is in a gaming session in which gaming data is exchanged between the mobile communication terminal and the at least one other terminal, and the sensor data is corresponded to and included in the gaming data.

19. A mobile communication terminal comprising:
at least one processor; and
at least one memory including computer program code,
the at least one memory and the computer program code configured to, with the at least one processor, cause the mobile communication terminal to perform at least the following,
couple with at least one sensor thereto;
capture data from the at least one sensor;
send the captured data to at least one other mobile communication terminal while receiving other sensor data from the at least one other mobile communication terminal; and
present an indication of the received other sensor data via a display or loudspeaker of the mobile communication terminal,
wherein the mobile communication terminal is in a gaming session in which gaming data is exchanged between the mobile communication terminal and the at least one other terminal, and the sensor data is corresponded to and included in the gaming data.

* * * * *